United States Patent [19]

Gadient et al.

[11] Patent Number: 4,855,288
[45] Date of Patent: Aug. 8, 1989

[54] NEW FURANURONIC ACID DERIVATIVES, PROCESS FOR THEIR PRODUCTION AND THEIR USE

[75] Inventors: Fulvio Gadient, Birsfelden; Arnold Vogel, Riehen, both of Switzerland

[73] Assignee: Sandoz Ltd., Basel, Switzerland

[21] Appl. No.: 132,492

[22] Filed: Dec. 14, 1987

[30] Foreign Application Priority Data

Dec. 15, 1986 [DE] Fed. Rep. of Germany ....... 3642748
Sep. 5, 1987 [DE] Fed. Rep. of Germany ....... 3729768

[51] Int. Cl.$^4$ ............ C07H 19/67; C07H 19/18; A61K 31/70; A61K 31/52
[52] U.S. Cl. .................. 514/45; 514/46; 536/24; 536/26
[58] Field of Search ............ 536/74, 76; 514/45, 514/46

[56] References Cited

U.S. PATENT DOCUMENTS

| | | | |
|---|---|---|---|
| 3,551,409 | 12/1970 | Kampe et al. | 536/26 |
| 3,966,917 | 6/1976 | Prasad et al. | 536/26 |
| 4,029,884 | 6/1977 | Stein et al. | 536/26 |

FOREIGN PATENT DOCUMENTS 2610985 9/1977 Fed. Rep. of Germany ........ 536/24
2730846 1/1978 Fed. Rep. of Germany ........ 536/24

*Primary Examiner*—Ronald W. Griffin
*Assistant Examiner*—L. Eric Crane
*Attorney, Agent, or Firm*—Gerald D. Sharkin; Robert S. Honor; Thomas O. McGovern

[57] ABSTRACT

1'-desoxy-1'-(6-amino-9-purinyl)-β-D-ribofuranuronic acid thioamides of formula

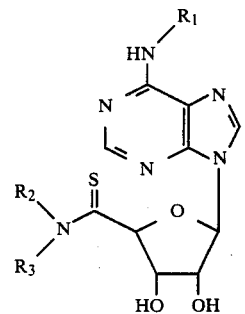

wherein $R_1$, $R_2$ and $R_3$ possess various definitions given in claim 2, are effective against raised blood pressure.

7 Claims, No Drawings

NEW FURANURONIC ACID DERIVATIVES, PROCESS FOR THEIR PRODUCTION AND THEIR USE

The present invention provides 1'-desoxy-1'-(6-amino-9-purinyl)-β-D-tribofuranuronic acid thioamides.

These compounds are called hereinafter compounds of the invention.

β-D-ribofuranuronic acid is also known as β-D-riburonic acid.

The compounds may be substituted where desired e.g. in free amino groups.

The invention especially provides 1'-desoxy-1'-(6-amino-9-purinyl)-β-D-ribofuranuronic acid thioamides of formula I,

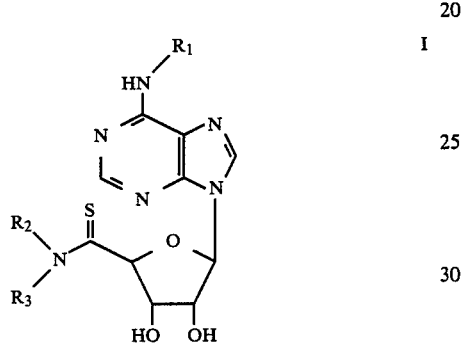

wherein $R_1$ signifies hydrogen, $(C_{1-6})$alkyl which may be optionally monosubstituted by a hydroxyl, a —SH—or a

group; $(C_{3-7})$alkenyl, $(C_{3-7})$alkinyl; $(C_{3-7})$cycloalkyl which may be optionally mono- or di-substituted by a hydroxyl, a —SH or a

'group, $(C_{3-7})$ cycloalkyl$(C_{1-3})$alkyl which may be optionally mono- or di-substituted in the cycloalkyl ring by a hydroxyl, a —SH or a

group; phenyl which may be optionally mono-, di- or tri-substituted by halogen with an atomic number of 9–35, $(C_{1-4})$alkyl, $(C_{1-4})$alkoxy, a hydroxyl, a —SH a —S—$(C_{1-4})$alkyl, a $SO_2$—$(C_{1-4})$alkyl or a

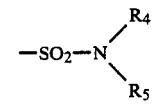

group; phenyl-$(C_{1-6})$ alkyl which may be optionally mono- or di-substituted in the phenyl ring by halogen with an atomic number of 9–35, $(C_{1-4})$alkyl, $(C_{1-4})$alkoxy, a hydroxyl, a —SH, a —S—$(C_{1-4})$alkyl, a $SO_2(C_{1-4})$alkyl or a

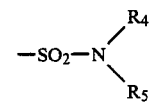

group, and wherein the $(C_{1-6})$alkylene chain may be optionally substituted by a hydroxyl group; phenyl-$(C_{3-7})$alkenyl which may be optionally substituted in the phenyl ring by halogen with an atomic number of 9–35, $(C_{1-4})$alkyl, $(C_{1-4})$-alkoxy, a hydroxyl, a —SH, a —S—$(C_{1-4})$alkyl, a —SO$_2$—$(C_{1-4})$alkyl or a

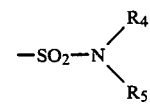

group; a 5 or 6 membered, monocyclic heteroaryl which contains either (i) one or two nitrogen atoms; or (ii) one oxygen atom or one sulphur atom and optionally one nitrogen atom, or a 5 or 6 membered, monocyclic heteroaryl-$(C_{1-5})$alkyl containing in the heteroaryl moiety either (i) one or two nitrogen atoms; or (ii) one oxygen atom or one sulphur atom and optionally one nitrogen atom and wherein the alkylene moiety may be optionally substituted by a hydroxyl group, and $R_2$ signifies hydrogen, $(C_{1-4})$alkyl which may be optionally mono-substituted by a hydroxyl, a —SH or a

group, or it signifies $(C_{3-6})$cycloalkyl, and $R_3$ is hydrogen or $(C_{1-4})$alkyl which may be optionally mono-substituted by a hydroxyl, a —SH or a

group, wherein $R_4$ and $R_5$ are the same or different and signify hydrogen or $(C_{1-4})$alkyl.

Of the compounds of formula I, preferred compounds possess the formula Ia,

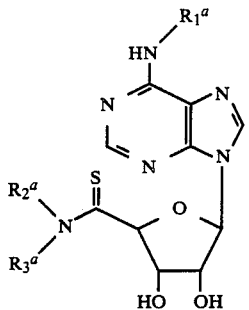

Ia wherein
$R_1^a$ signifies $(C_{3\text{-}7})$cycloalkyl which may be optionally mono or di-substituted by a hydroxyl, a —SH or a

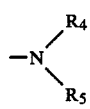

group; phenyl-$(C_{1\text{-}6})$-alkyl which may be mono- or di-substituted in the phenyl ring by halogen with an atomic number of 9–35, $(C_{1\text{-}4})$alkyl, $(C_{1\text{-}4})$alkoxy, a hydroxyl, a —SH, a —S—$(C_{1\text{-}4})$alkyl, a —SO$_2$—$(C_{1\text{-}4})$-alkyl or a

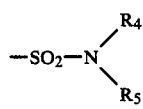

group, wherein the $(C_{1\text{-}6})$alkylene chain may be optionally substituted by a hydroxyl group; or phenyl which may be optionally mono-, di- or tri-substituted by halogen with an atomic number of 9–35, $(C_{1\text{-}4})$alkyl, $(C_{1\text{-}4})$alkoxy, a hydroxyl, a —SH, a —S—$(C_{1\text{-}4})$alkyl, a —SO$_2$—$(C_{1\text{-}4})$alkyl or a

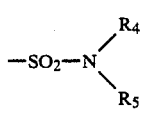

group,
$R_2^a$ is hydrogen, $(C_{1\text{-}4})$alkyl which may be optionally mono-substituted by a hydroxyl, a —SH or a

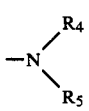

group, or $(C_{3\text{-}6})$cycloalkyl, and
$R_3^a$ is hydrogen or $(C_{1\text{-}4})$alkyl which may be optionally mono-substituted by a hydroxyl, a —SH or a

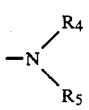

group, wherein $R_4$ and $R_5$ are respectively defined as above.

Of the compounds of formula I, especially preferred compounds possess the formula Ib,

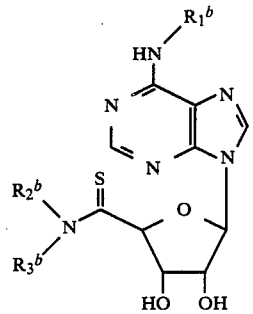

Ib wherein
$R_1^b$ signifies $(C_{3\text{-}7})$cycloalkyl which may be optionally mono- or di-substituted by a hydroxyl, a —SH or a

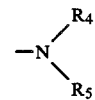

group, or phenyl-$(C_{1\text{-}6})$-alkyl which may be optionally mono- or di-substituted in the phenyl ring by halogen with an atomic number of 9–35, $(C_{1\text{-}4})$alkyl, $(C_{1\text{-}4})$alkoxy, a hydroxyl, a —SH, a —S—$(C_{1\text{-}4})$alkyl, a —SO$_2$—$(C_{1\text{-}4})$alkyl or a

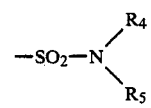

group, wherein the $(C_{1\text{-}6})$alkylene chain may be optionally substituted by a hydroxyl group,
$R_2^b$ is $(C_{1\text{-}4})$alkyl which may be optionally mono-substituted by a hydroxyl, a —SH or a

group, or it is $(C_{3\text{-}6})$cycloalkyl, and
$R_3^b$ is hydrogen, whereby $R_4$ and $R_5$ are respectively defined as above.

In formula I, halogen with an atomic number of 9–35 denotes fluorine, chlorine or bromine, preferably fluorine or chlorine, a $(C_{1\text{-}4})$-alkyl group is methyl, ethyl, n-propyl, i-propyl, n-butyl, i-butyl, tert.-butyl, and if it contains up to 6 carbon atoms, it is also n-pentyl, i-pentyl, n-hexyl, i-hexyl, etc., especially methyl, a $(C_{1\text{-}4})$-alkoxy group is methoxy, ethoxy, n-propoxy, i-propoxy, n-butoxy, i-butoxy, tert.-butoxy, and if it contains up to 6 carbon atoms, it is also n-pentoxy, i-pentoxy, n-hexoxy, i-hexoxy etc., especially methoxy, $(C_{3\text{-}7})$alkenyl is methallyl, butenyl, pentenyl etc., whereby the chain may be straight or branched and the double bond may be found in various positions, but preferably not adjacent to nitrogen, $(C_{3\text{-}7})$alkinyl is propinyl, butinyl, pentinyl, hexinyl, whereby the chain may be straight or branched and the triple bond may be found in various positions, but preferably not adjacent to nitrogen. $(C_{3-7})$cycloalkyl signifies cyclopropyl, cyclobutyl, cyclopentyl, cyclohexyl or cycloheptyl. If it is substituted, the substituents are in o-, p- or m-position, but preferably either when disubstituted in o-, o'-position, or when monosubstituted in p-position. For example $(C_{3-7})$cycloalkyl$(C_{1-3})$alkyl may denote the above-mentioned cycloalkyl and alkyl radicals, to which as indicated above substituents may be attached. Substitution of the phenyl ring may take place in o-, m- or p-position, and when disubstituted these are preferably in the m- and p-positions, and when monosubstituted this is preferably in p-position. In cycloalkyl and phenylalkyl, the alkyl radicals are as discussed above. If the phenyl ring is di-substituted, the substituents are preferably bonded in the m- and p-position, and when monosubstituted in p-position. An alkylene group may be branched or contain a straight chain.

The compounds according to the invention are obtained e.g. by cleavage of an isopropylidene group from 1'-desoxy-1'-(6-amino-9-purinyl)-2',3'-isopropylidene-β-D-ribofuranuronic acid thioamides e.g. of formula II

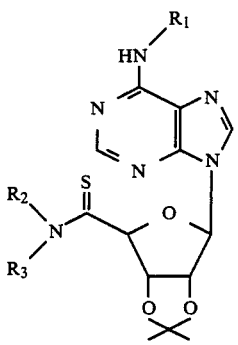

wherein $R_1$, $R_2$ and $R_3$ have the definitions given above.

The above process conveniently takes place by treating compounds of formula II with an agent which cleaves the isopropylidene group. Trifluoroacetic acid has proved to be especially suitable for this. A further cleavable agent is aqueous hydrochloric acid or aqueous formic acid.

The compounds of formula II used as starting compounds are obtained by means of thianation of compounds of formula III,

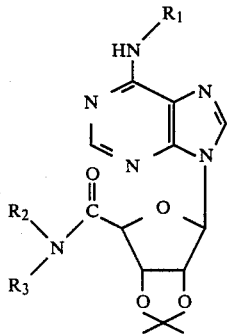

wherein $R_1$, $R_2$ and $R_3$ are defined as above.

The above-described thianation process is suitably effected using known thianation agents, for example hydrogen sulphide, phosphorus pentasulphide or LAWESSON'S REAGENT (p-methoxy-phenylthiophosphine sulphide dimer). The last named reagent is preferred. The reaction itself takes place in known manner. If for example hydrogen sulphide is used, an acid such as hydrochloric acid is conveniently added in catalytic doses, and the reaction is carried out in a polar solvent such as acetic acid or ethanol. When using LAWESSON'S REAGENT, the reaction is conveniently carried out in a dry solvent such as toluene or methylene chloride.

If in the compounds of formula I there are sufficiently basic groups present e.g. $R_1$ denotes a $(C_{1-6})$alkyl group which is substituted by a

group, these compounds can form salts forms with strong acids. Preferred salts are the hydrochlorides, hydrobromides or fumarates.

The compounds of the invention may be purified by known procedures e.g. column chromatography or high pressure chromatography.

Insofar as the production of the required starting materials is not described, these are known (e.g. from WO 86/00310) or may be produced by known processes, or analogously to the processes described here, or analogously to known processes.

In the following examples, all temperatures are given in degrees celsius and are uncorrected.

EXAMPLE 1

1'-desoxy-1'-(6-cyclopentylamino-9-purinyl)-β-D-ribofuranuronic acid-N-ethylthioamide 1.3 g of 1'-desoxy-1'-(6-cyclopentylamino-9-purinyl)-2',3'-isopropylidene-β-D-ribofuranuronic acid-N-ethylthioamide are dissolved at 0° in 10 ml of 90% trifluoroacetic acid, and the solution is left to stand for 1 hour. Then, the solution is totally concentrated under reduced pressure, and the residue is partitioned between ethyl acetate and diluted, aqueous ammonia. After washing with saturated sodium chloride solution, the product is dried over sodium sulphate, filtered and the filtrate is totally concentrated. The residue is then purified by chromatography on silica gel with ethyl acetate. The pure fractions are collected, concentrated and pulverised.

The end product dissolves at 105°–110°.

Rf in ethyl acetate: 0.4.

The 1'-desoxy-1'-(6-cyclopentylamino-9-purinyl)-2',3'-isopropylidene-β-D-ribofuranuronic acid-N-ethylthioamide used as the starting material can be produced e.g. as follows:

2g of 1'-desoxy-1'-(6-cyclopentylamino-9-purinyl)-2',3'-isopropylidene-β-D-ribofuranuronic acid-N-ethylamide (produced in accordance with the process described in PCT application WO 86/00310) are stirred for half an hour with 0.97 g of a Lawesson's reagent in 48 ml of toluene in an oil bath of 100°. After cooling, the toluene phase is washed with water and dried over sodium sulphate. After filtration, the product is concentrated under reduced pressure, and the residue is chromatographed on silica gel with ethyl acetate as the eluant. The pure fractions which have evaporated to a colourless foam have a Rf of 0.7 in ethyl acetate.

Analogously to example 1, the following compounds of formula I are obtained, in which $R_1$, $R_2$ and $R_3$ are defined as follows:

| Example | $R_1$ | $R_3$ | $R_2$ | m.p. |
|---|---|---|---|---|
| 2 | H | H | Et | 137–140° |
| 3 | (R)—PhCH$_2$CH(CH$_3$)— | H | Et | 131–133° |
| 4 | 4-CH$_3$O—C$_6$H$_4$— | H | Et | 135–137° |
| 5 | Me— | H | Et | 135–140° |
| 6 | 4-HO—C$_6$H$_4$— | H | Et | 191–194° |
| 7 | Ph—CH=CH—CH$_2$— | H | Et | 158–163° |
| 8 | Cyclopentyl— | Me | Me | 107–111° |
| 9 | Cyclopentyl | H | H | 139–143° |
| 10 | 4-Cl—C$_6$H$_4$— | H | Et | 267–272° |
| 11 | 4-Me—C$_6$H$_4$— | H | Et | 126–130° |
| 12 | 3,4,5-tri-MeO—C$_6$H$_2$— | H | Et | 254–257° |
| 13 | Cyclopentyl | H | Cyclopropyl | 132–136° |
| 14 | CH$_2$CH$_2$OH | H | Et | 214–218° |
| 15 | 3-Pentyl | H | Et | 146–148° |
| 16 | Phenethyl | H | Et | 169–172° |
| 17 | 3,4-di-MeO—phenethyl | H | Et | 125–130° |
| 18 | 4-MeS—C$_6$H$_4$— | H | Et | 210–214° |
| 19 | 4-MeSO$_2$—C$_6$H$_4$— | H | Et | 180–184° |
| 20 | 4-H$_2$NSO$_2$—C$_6$H$_4$— | H | Et | 163–167° |
| 21 | Cyclopropylmethyl— | H | Et | 117–122° |
| 22 | 4-H$_2$NSO$_2$-phenethyl | H | Et | 135–140° |
| 23 | (R)—2-Butyl | H | Et | 159–161° |
| 24 | (S)—2-Butyl | H | Et | 181–183° |
| 25 | 2-Dimethylaminoethyl | H | Et | FOAM |
| 26 | Allyl | H | Et | 139–142° |
| 27 | Propargyl | H | Et | 197–199° |
| 28 | 3-F—C$_6$H$_4$— | H | Et | 194–196° |

The compounds according to the invention exhibit pharmacological activity. They are therefore useful as medicaments.

In particular, the compounds according to the invention have anti-hypertensive activity, as indicated from the results of the following trials:

Measurement of the binding to adenosine A1 and A2 receptors in membranes from the rat's cortex or from the cerebral cortex or striatum of the pig, using the method of R. F. BRUNS, G. H. LU and T. A. PUGSLEY, which is described in MOLEC. PHARMACOL. 29, 331–346 (1986). The compounds bind to the A1 receptors at concentrations from ca. $10^{-7}$ molar to $10^{-6}$ molar. The compounds bind to the A2 receptors at concentrations from ca. $10^{-6}$ molar to $10^{-5}$ molar. The A1 to A2 selectivity amounts to 210.

Measurement of blood pressure, heart rate, urine production and renin activity in the plasma of wake, NaCl-depleted, normotensive or spontaneously hypertensive rats which have catheters implanted in the abdominal aorta and the Vena cava, following i.v. and p.o. administration or administration of the compounds according to the invention as an infusion or a bolus, according to the method of J. F. M. SMITS and J. M. BRODY described in Am. J. Physiol. 247, R1 003–R1 008 (1984). The compounds are active as blood pressure lowering agents at a dose of from about 10 to about 100 microgram/kg i.v. and from 0.1 to 1 mg/kg p.o.

Further testing of the activity of the compounds of the invention on the isolated, perfused rat's kidneys for the following parameters:
renin secretion
renal haemodynamics (vasodilation) and
inhibition of the release of noradrenaline from nerve ends following electro-stimulation of the renal nerves according to the method of H. J. SCHUREK, J. P. BRECHT, H. LOHFERT and K. HIERHOLZER, described in Pflüger's Arch. 354, 349–65 (1975), as well as P. M. VANHOUETTE, D. BROWNING, E. COEN, T. J. VERBEUREN, L. ZONNEKEYEN and M. G. COLLIS described in HYPERTENSION 4, 251–256 (1982).

From the results of the trials, it is indicated that both an inhibition of renin secretion and of the release of noradrenaline from nerve ends, and direct vasodilation, contribute towards the anti-hypertensive activity of the compounds according to the invention. From this, it is evident that the compounds according to the invention are useful as anti-hypertensive agents, but also to effect coronary vasodilation, protect the vascular endothelium both by inhibiting platelet aggregation and activated leucocytes, as well as to reduce blood lipids and improve glucose tolerance.

For the above indications, of the compounds according to the invention, the compound of example 15 is preferred.

For the above-mentioned indictions particularly as anti-hypertensive agents, the exact dosage to be used of course varies according to the substance used, the host, the mode of administration and the desired treatment. In general however, satisfactory results are obtained with a daily dosage of approximately 0.01 to about 10 mg per kg body weight; if necessary, administration may take place in 2 or 4 divided doses or in sustained release form. In larger mammals, for example humans, the daily dosage is in the range of approximately 10 to 500 mg; suitable dosage forms for e.g. oral or parenteral administration generally contain about 5 to 250 mg, together with solid or liquid carrier substances.

The preferred compound of example 15 for the anti-hypertensive indication exhibits at a dose of 0.4 mg/kg p.o. in the above mentioned rat blood pressure lowering test a lowering of 31 mm Hg in systolic blood pressure and 65 mm Hg in diastolic blood pressure. The mean arterial pressure is reduced by 49 mm Hg. It is therefore indicated that the compound of example 15 may be administered at daily dosages of from 10 to 50 mg p.o.

The compounds according to the invention may be administered alone or in suitable dosage form. The medicinal forms, e.g. a solution or a tablet, can be produced analogously to known methods.

The compounds of the invention may be administered in pharmaceutically acceptable form e.g. in free form or when sufficiently basic groups exist in pharmaceutically acceptable acid addition salt forms.

The invention therefore provides pharmaceutical compositions which contain the compounds according to the invention in association with a pharmaceutically acceptable adjuvant and/or diluent. They can be produced by using conventional pharmaceutical adjuvants and carriers in conventional manner.

The present invention also provides (i) the use of a compound of the invention in the treatment of raised blood pressure and (ii) the use of a compmound of the invention in the manufacture of a medicament suitable for treating raised blood pressure.

What we claim is:

1. A 1'-desoxy-1'-(6-amino-9-purinyl)-β-D-ribofuranuronic acid thioamide of formula I,

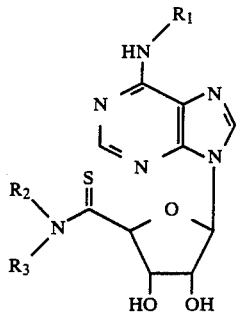 I wherein
R₁ signifies hydrogen; $(C_{1-6})$alkyl which may be monosubstituted by a hydroxyl, a —SH or a

group; $(C_{3-7})$alkenyl; $(C_{3-7})$alkinyl; $(C_{3-7})$cycloalkyl which may be mono- or di-substituted by a hydroxyl, a —SH or a

group; $(C_{3-7})$ cycloalkyl$(C_{1-3})$alkyl which may be mono- or di-substituted in the cycloalkyl ring by a hydroxyl, a —SH or a

group; phenyl which may be mono-, di- or tri-substituted by halogen with an atomic number of 9–35, $(C_{1-4})$alkyl, $(C_{1-4})$alkoxy, a hydroxyl-, a —SH, a —S—$(C_{1-4})$alkyl, a $SO_2$—$(C_{1-4})$alkyl or a

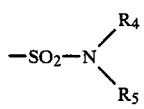

group; phenyl-$(C_{1-6})$ alkyl which may be mono- or di-substituted in the phenyl ring by halogen with an atomic number of 9–35, $(C_{1-4})$alkyl, $(C_{1-4})$alkoxy, a hydroxyl, a —SH, a —S—$(C_{1-4})$alkyl, a $SO_2(C_{1-4})$alkyl or a

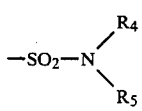

group, and wherein the $(C_{1-6})$alkylene chain may be substituted by a hydroxyl gorup, phenyl-$(C_{3-7})$alkenyl which may be substituted in the phenyl ring by halogen with an atomic number of 9–35, $(C_{1-4})$alkyl, $(C_{1-4})$-alkoxy, a hydroxyl, a —SH—, a —S—$(C_{1-4})$alkyl-, a —$SO_2$—$(C_{1-4})$alkyl or a

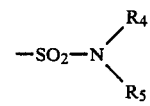

group; a 5 or 6 membered, monocyclic heteroaryl which (i) contains one or two nitrogen atoms or (ii) one oxygen atom or one sulphur atom or (iii) one oxygen atom or one sulphur atom and one nitrogen atom, or a 5 or 6 membered, monocyclic heteroaryl-$(1-5)$alkyl containing in the heteroaryl moiety either (i) one or two nitrogen atoms (ii) one oxygen atom or one sulphur atom or (iii) one oxygen atom or one sulphur atom and one nitrogen atom; wherein the alkylene moiety may be substituted by a hydroxyl group, and
R₂ signifies hydrogen, $(C_{1-4})$alkyl which may be mono-substituted by a hydroxyl, a —SH or a

group, or it signifies $(C_{3-6})$cycloalkyl, and
R₃ is hydrogen or $(C_{1-4})$alkyl which may be monosubstituted by a hydroxyl, a —SH or a

group, whereby R₄ and R₅ are independently hydrogen or $(C_{1-4})$alkyl.

2. Compounds of formula Ia,

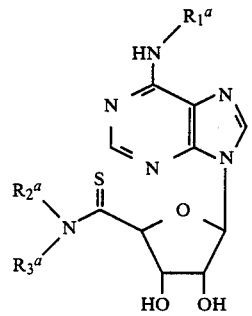 Ia wherein
R₁ᵃ signifies $(C_{3-7})$cycloalkyl which may be mono or di-substituted by a hydroxyl, a —SH or a

group; phenyl-$(1-6)$-alkyl which may be mono- or di-substituted in the phenyl ring by halogen with an atomic number of 5–35, $(C_{1-4})$alkyl, $(C_{1-4})$alkoxy, a hydroxyl, a —SH, a —S—($C_{1-4}$)alkyl, a —$SO_2$—($C_{1-4}$)-alkyl or a

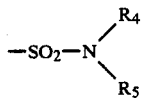

group, wherein the ($C_{1-6}$)alkylene chain may be substituted by a hydroxyl gorup; or phenyl which may be mono-, di- or tri-substituted by halogen with an atomic number of 9–35, ($C_{1-4}$)alkyl, ($C_{1-4}$)alkoxy, a hydroxyl, a —SH, a —S—($C_{1-4}$)alkyl, a —$SO_2$—($C_{1-4}$)alkyl or a

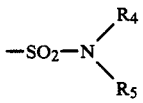

group,
$R_2{}^a$ is hydrogen, ($C_{1-4}$)alkyl which may be mono-substituted by a hydroxyl, a —SH or a

group, or ($C_{3-6}$)cycloalkyl, and
$R_3{}^a$ is hydrogen or ($C_{1-4}$)alkyl which may be mono-substituted by a hydroxyl, a —SH or a

group, wherein $R_4$ and $R_5$ are respectively defined as in claim 1.

3. Compounds of formula Ib,

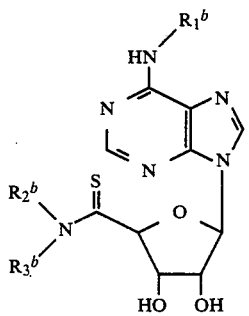

wherein
$R_1{}^b$ signifies ($C_{3-7}$)cycloalkyl which may be mono- or di-substituted by a hydroxyl, a —SH or a

group, or phenyl-($C_{1-6}$)-alkyl which may be mono- or di-substituted in the phenyl ring by halogen with an atomic number of 9–35, ($C_{1-4}$)alkyl, ($C_{1-4}$)alkoxy, a hydroxyl, a —SH, a —S—($C_{1-4}$)alkyl, a —$SO_2$—($C_{1-4}$)alkyl or a

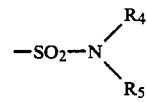

group, wherein the ($C_{1-6}$)alkylene chain may be substituted by a hydroxyl group,
$R_2{}^b$ is ($C_{1-4}$)alkyl which may be mono-substituted by a hydroxyl, a —SH or a

group, or it is ($C_{3-6}$)cycloalkyl, and
$R_3{}^b$ is hydrogen, whereby $R_4$ and $R_5$ are respectively defined as in claim 1.

4. 1'-desoxy-1'-(6-(3-pentyl)-amino-9-purinyl)-β-D-ribofuranuronic acid-N-ethylthioamide.

5. Compound according to claim 1 chosen from:
1'-desoxy-1'-(6-cyclopentylamino-9-purinyl)-β-D-ribofuranuronic acid-N-ethylthioamide;
1'-desoxy-1'-(6-amino-9-purinyl)-β-D-ribofuranuronic acid-N-ethylthioamide;
1'-desoxy-1'-(6-[phenylisopropyl]amino-9-purinyl)-β-D-ribofuranuronic acid-N-ethylthioamide;
1'-desoxy-1'-(6-(4-methoxy-phenyl)-amino-9-purinyl)-β-D-ribofuranuronic acid-N-ethylthioamide;
1'-desoxy-1'-(6-methylamino-9-purinyl)-β-D-ribofuranuronic acid-N-ethylthioamide;
1'-desoxy-1'-(6-(4-hydroxyphenyl)-amino-9-purinyl)-β-D-ribofuranuronic acid-N-ethylthioamide;
1'-desoxy-1'-(6-cinnamylamino-9-purinyl)-β-D-ribofuranuronic acid-N-ethylthioamide;
1'-desoxy-1'-(6-cyclopentylamino-9-purinyl)-β-D-ribofuranuronic acid-N,N-dimethylthioamide;
1'-desoxy-1'-(6-cyclopentylamino-9-purinyl)-β-D-ribofuranuronic acid-N-thioamide;
1'-desoxy-1'-(6-(4-chlorophenyl)-amino-9-purinyl)-β-D-ribofuranuronic acid-N-ethylthioamide;
1'-desoxy-1'-(6-(4-methylphenyl)-amino-9-purinyl)-β-D-ribofuranuronic acid-N-ethylthioamide;
1'-desoxy-1'-(6-(3,4,5-trimethoxyphenyl)-amino-9-purinyl)-β-D-ribofuranuronic acid-N-ethylthioamide;
1'-desoxy-1'-(6-cyclopentylamino-9-purinyl)-β-D-ribofuranuronic acid-N-cyclopropylthioamide;
1'-desoxy-1'-(6-β-hydroxyethylamino-9-purinyl)-β-D-ribofuranuronic acid-N-ethylthioamide;
1'-desoxy-1'-(6-(3-pentyl)-amino-9-purinyl)-β-D-ribofuranuronic acid-N-ethylthioamide;
1'-desoxy-1'-(6-phenethylamino-9-purinyl)-β-D-ribofuranuronic acid-N-ethylthioamide;
1'-desoxy-1'-(6-(3,4-dimethoxyphenethyl)-amino-9-purinyl)-β-D-ribofuranuronic acid-N-ethylthioamide;
1'-desoxy-1'-(6-(4-methylthiophenyl)-amino-9-purinyl)-β-D-ribofuranuronic acid-N-ethylthioamide;
1'-desoxy-1'-(6-(4-methylsulfonylphenyl)-amino-9-purinyl)-β-D-ribofuranuronic acid-N-ethylthioamide;

1'-desoxy-1'-(6-(4-sulfamoylphenyl)-amino-9-purinyl)-β-D-ribofuranuronic acid-N-ethylthioamide;

1'-desoxy-1'-(6-(2-dimethylaminoethyl)-amino-9-purinyl)-β-D-ribofuranuronic acid-N-ethylthioamide;

1'-desoxy-1'-(6-allylamino-9-purinyl)-β-D-ribofuranuronic acid-N-ethylthioamide;

1'-desoxy-1'-(6-propargylamino-9-purinyl)-β-D-ribofuranuronic acid-N-ethylthioamide;

1'-desoxy-1'-(6-(3-fluorophenyl)-amino-9-purinyl)-β-D-ribofuranuronic acid-N-ethylthioamide;

1'-desoxy-1'-(6-cyclopropyl-methylamino-9-purinyl)-β-D-ribofuranuronic acid-N-ethylthioamide;

1'-desoxy-1'-(6-(4-sulfamoylphenethyl)-amino-9-purinyl)-D-β-ribofuranuronic acid-N-ethylthioamide;

1'-desoxy-1'-(6-((R)-2-butyl)-amino-9-purinyl)-β-D-ribofuranuronic acid-N-ethylthioamide;

1'-desoxy-1'-(6-((S)-2-butyl)-amino-9-purinyl)-β-D-ribofuranuronic acid-N-ethylthioamide.

6. A method of treatment of a raised blood pressure which comprises administering to a subject in need of such a treatment a therapeutically effective amount of a compound of formula I according to claim 1.

7. A pharmaceutical composition useful in treating hypertension comprising an antihypertensive effective amount of a compound of claim 1 and a pharmaceutically acceptable carrier therefor.

* * * * *